US008715238B2

(12) United States Patent
Silver

(10) Patent No.: US 8,715,238 B2
(45) Date of Patent: May 6, 2014

(54) PUMPING DEVICE, AS FOR ENTERAL FEEDING ASSEMBLY

(75) Inventor: Brian H. Silver, Cary, IL (US)

(73) Assignee: Medela Holding AG, Baar (CH)

( * ) Notice: Subject to any disclaimer, the term of this patent is extended or adjusted under 35 U.S.C. 154(b) by 116 days.

(21) Appl. No.: 13/189,196

(22) Filed: Jul. 22, 2011

(65) Prior Publication Data

US 2012/0022451 A1 Jan. 26, 2012

Related U.S. Application Data

(60) Provisional application No. 61/367,283, filed on Jul. 23, 2010, provisional application No. 61/367,272, filed on Jul. 23, 2010.

(51) Int. Cl.
*A61M 1/00* (2006.01)

(52) U.S. Cl.
USPC .......... 604/151

(58) Field of Classification Search
USPC .......... 604/410, 411, 249, 246, 256, 910, 604/131–157
See application file for complete search history.

(56) References Cited

U.S. PATENT DOCUMENTS 5,785,688 A 7/1998 Joshi et al.
7,029,245 B2 * 4/2006 Maianti et al. .......... 417/395
7,255,681 B1 * 8/2007 Silver et al. .......... 604/74
7,270,648 B2 * 9/2007 Kazemzadeh .......... 604/135
7,753,884 B2 7/2010 Gallnbock
2005/0215850 A1 9/2005 Klein et al.
2008/0183153 A1 * 7/2008 Enns .......... 604/533
2008/0195047 A1 * 8/2008 Price .......... 604/151

OTHER PUBLICATIONS

International Search Report and Written Opinion for International App. No. PCT/US2011/045068, mailed Feb. 29, 2012.

* cited by examiner

*Primary Examiner* — Nicholas Lucchesi
*Assistant Examiner* — Pritesh Patel
(74) *Attorney, Agent, or Firm* — McDonnell Boehnen Hulbert & Berghoff LLP

(57) ABSTRACT

A pumping device is disclosed, as for use with an enteral feeding assembly. In one form the pumping device is a diaphragm pump including a first dome portion, a second dome portion, and a flexible membrane located between the first and second dome portions. A pressure differential is created between the two chambers thus created by membrane, so as to meter fluid (to be delivered) to a patient. The fluid to be delivered may be located in one of the chambers. A portable fluid pump is also provided including a syringe and spring pump drive mechanism mounted in a casing. The spring pump drive mechanism has two piston devices in fluid communication with each other. As one piston device moves in one direction within its associated driving barrel, it serves to drive the other piston device.

31 Claims, 10 Drawing Sheets

PUMPING DEVICE, AS FOR ENTERAL FEEDING ASSEMBLY

CROSS REFERENCE TO RELATED APPLICATIONS

This application claims priority to U.S. Provisional Application Nos. 61/367,283 filed on Jul. 23, 2010 and 61/367,272 filed on Jul. 23, 2010, the entire contents of both are incorporated by reference herein.

FIELD OF THE INVENTION

The present invention relates generally to a portable pumping apparatus, and more particularly in one aspect to a pumping device for use with an enteral feeding assembly.

BACKGROUND OF THE INVENTION

Fluid delivery systems, such as feeding tubes, are used to deliver nutrients and medicine to patients. The state of being fed by a feeding tube is known in the art as enteral feeding or tube feeding.

As an example, in a neo-natal unit, infants are often fed enterally. A tube is inserted in the mouth or nasal opening of the infant and through the esophagus for delivery of the fluid to the stomach or intestinal region of the body. In this example, breast milk or formula are delivered by syringe (or some other container) into an enteral delivery system, such as an enteral tube, for delivery to the infant's stomach. However, enteral feeding systems can also be for pediatric or adult use. Sometimes a peristaltic pump is used to deliver fluids from a feeding bag.

Current pumping devices may be large and bulky, and often need to be plugged into an electrical outlet to function. They can require some nearby stand or pole for support, which adds to a cumbersome assembly. Further, the tubing may be of significant length to reach from the pumping device to the infant, which is not desirable.

SUMMARY OF THE INVENTION

The present invention in one embodiment provides a portable non-electric pumping device for delivery of fluid. The pumping device in one form is a diaphragm pump connectable to an enteral feeding tube. The diaphragm pump has a first dome portion, a second dome portion, and a flexible membrane located in between and separating the first and second dome portions, thus forming first and second chambers on opposite sides of the flexible membrane. In one embodiment, a vacuum source is connected to the pumping device to create a vacuum between the first dome portion and the flexible membrane in the first chamber. Fluid to be delivered is sucked into the second chamber formed by the flexible membrane and the second dome portion, through use of the vacuum source, as it moves the membrane or diaphragm from one side to the other of the device. The vacuum source is then disconnected with the first chamber sealed. The pumping device then functions to deliver and regulate fluid to the patient, by virtue of the flexible membrane returning to its original (rest) state, via an air vent device allowing air to slowly enter the first chamber, with fluid outflow either through the same inflow part, or some other outflow port. As secondary mechanism, such as a spring pushing the diaphragm, may also be used.

In an alternative embodiment, one of the chambers could be pressurized with an over-pressure, but function to deliver fluid in a similar manner. The pressure source could further be air, another gas, or a fluid such as a liquid, e.g., water or even the material to be delivered to the patient.

The present invention in another embodiment also provides a portable pumping mechanism. The pump includes a syringe and a spring-loaded pump drive mechanism mounted in a casing. The pump drive mechanism preferably includes a drive control mechanism that has two piston devices, such as two syringe or syringe-like devices, in fluid communication with each other, such as using water as the fluid. As one piston device moves in one direction, it serves to drive the other piston device. The plunger of the syringe is slaved to the piston of one of the piston devices, to discharge feed as that piston moves. A spring drive serves as the motive source for driving the piston devices. A pneumatic application (instead of water) of the pumping mechanism is further contemplated.

The pumping device may further include a volume indicator for measuring the amount of feeding fluid in the pumping device or the amount of feeding fluid that has been fed from the pumping device.

In yet another embodiment, one or more flexible bags or balloon-like structures may be placed within or attached to the pumping device. The flexible bag may also act as the pressure source to the pumping device.

Thus, in a very broad sense, the present invention provides a pumping device for enteral feeding which is placeable in the NICU bed, and most preferably does not utilize any electrically-driven motive parts for delivery of feed.

These and other features and advantages of the present invention will be further understood and appreciated when considered in relation to the following detailed description of embodiments of the invention, taken in conjunction with the drawings, in which:

DETAILED DESCRIPTION OF EMBODIMENTS OF THE INVENTION

Figure 1:
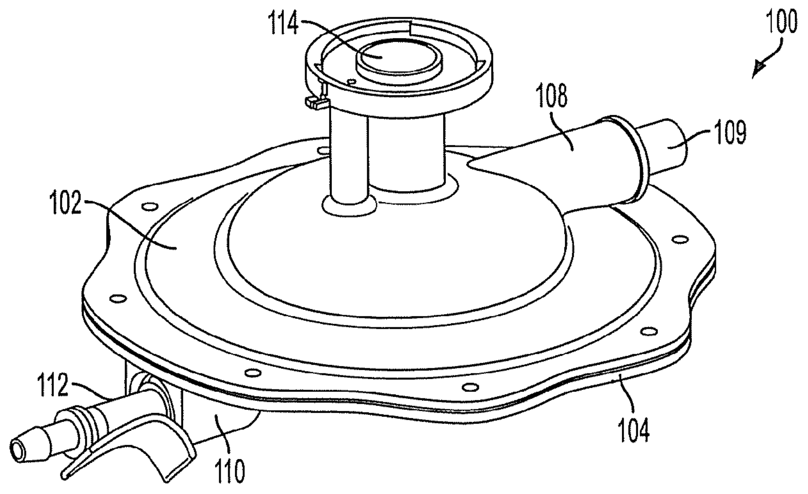
FIG. 1 is a perspective view of an embodiment of a pumping device according to certain aspects of the present invention.

One embodiment of the invention is shown in a pumping device of FIG. 1. This type of pumping device in the form of a diaphragm pump is simply illustrative, and not intended to be limiting of the invention. Referring to FIG. 1, a pumping device 100 includes a first dome portion 102 attached to a second dome portion 104. The first and second dome portions 102, 104 are secured to each other by a snap-fit connection, screws, rivets, ultrasonic welding, or some other known manner. It should be understood that the first and second dome portions 102, 104 may be secured by any suitable fastening mechanism, most preferably easily disassembled for cleaning. In some embodiments, the pumping device 100 may be spring-loaded. It may be made to be disposable.

Figure 2:
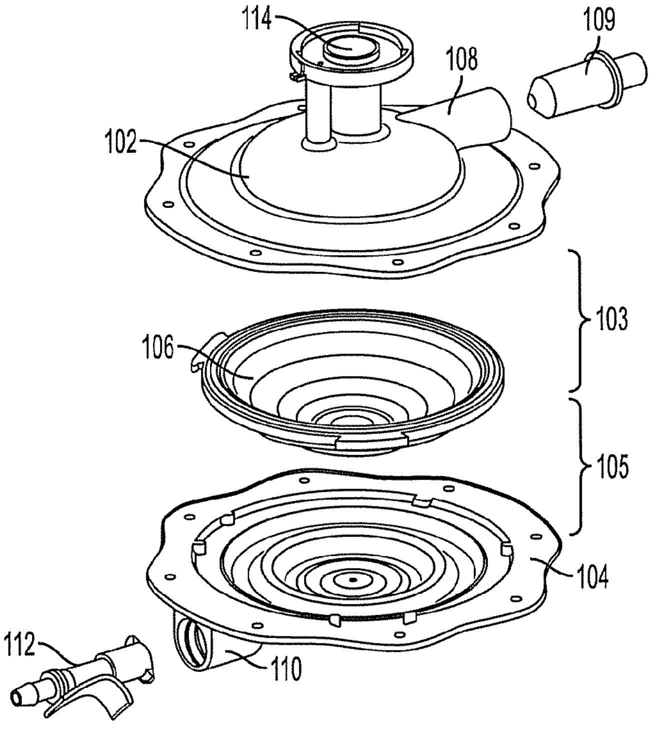
FIG. 2 is an exploded view of the pumping device shown in FIG. 1.

A flexible membrane or diaphragm 106 is placed between the first and second dome portions 102, 104, as shown in FIG. 2, and is held in place sandwiched between the two dome portions around the membrane edge. Thus, a first space or chamber 103 is created between the first dome portion 102 and the flexible membrane 106, and a second space or chamber 105 is created between the second dome portion 104 and the flexible membrane 106. The first and second dome portions 102, 104 are made of any suitable rigid material, such as plastic, for example. In some embodiments, as further discussed hereafter, one or both of the dome portions 102, 104 may be made of a flexible, stretchable material. The membrane 106 is flexible, made of silicone, rubber, or the like (although it could be a thin metal or other material, also).

Figure 3:
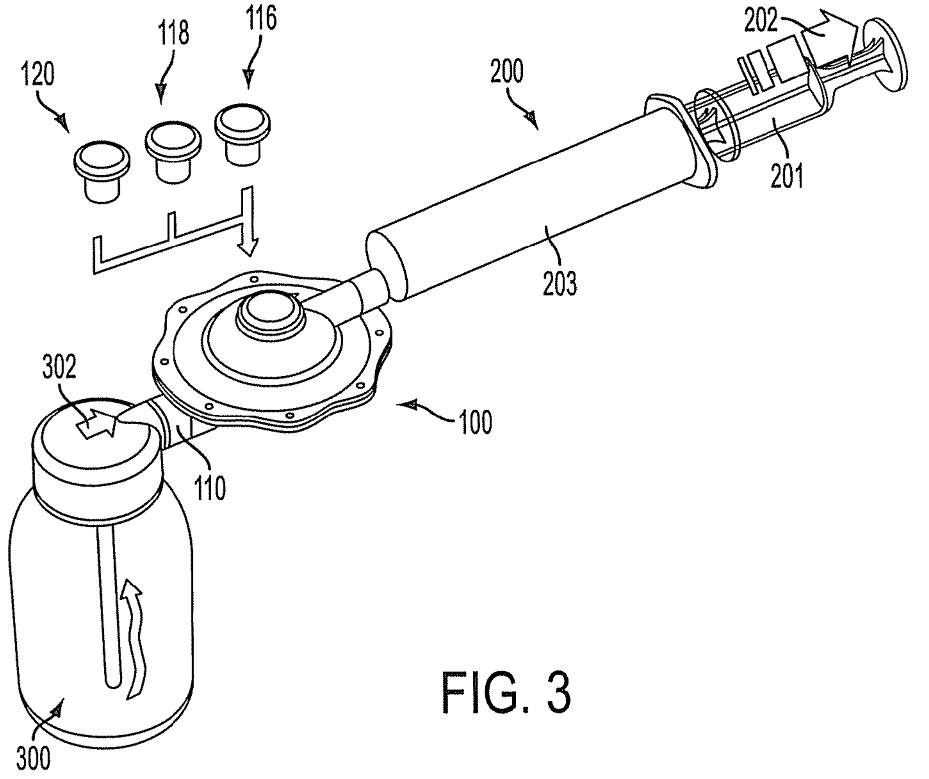
FIG. 3 is a perspective view of the pumping device of FIG. 1 connected to a vacuum source and container.

The first dome portion 102 may include a first port 108 for receiving a vacuum source 200, such as a syringe as shown in FIG. 3. The vacuum source 200 creates a vacuum in first chamber 103 between the first dome portion 102 and the flexible membrane 106, thereby causing the flexible membrane 106 to act as a driving force and move toward the first dome portion 102 into an expanded (distended) position. Here, the vacuum is provided by pulling the syringe piston 201 outwardly from within the syringe barrel 203. Thus, the volume of the first chamber 103 is reduced and the volume of the second chamber 105 is increased. The first port 108 includes a one-way valve 109, such as a duckbill valve or a reed valve, for example, to prevent air from escaping back through the first port 108 when the syringe (vacuum source) is removed. Specifically, a syringe actuated valve such as those produced by Halkey Roberts may be used.

Figure 4:
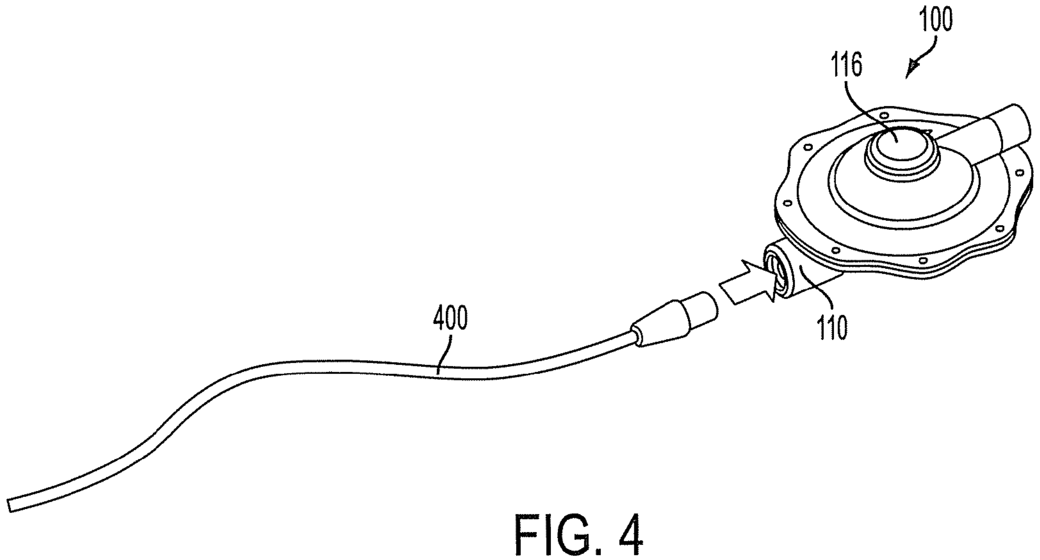
FIG. 4 is a perspective view of the pumping device of FIG. 1 connected to an enteral feeding tube.

For example, a syringe actuated valve may be removably attachable to a tube section, such as enteral feeding tube 400 shown in FIG. 4. Thus, when either a cap or syringe is pushed into the valve, a flexible element is collapsed upon itself, opening a channel into the top of the valve. The cap may comprise an orifice or other means to allow air into the valve. Fluid, such as enteral feed, may then flow into the valve and tubing, or air may be allowed to exit for venting. The valve has the flexible element in a chamber. The flexible member has scalloped areas and is fixed at a distal end, but free to move longitudinally at a proximal end. The proximal end is located within a top disk of the valve structure, and closes an orifice therein. When pressed by a syringe-tip, for example, the proximal end moves distally, opening the orifice. The valve may be a 245 series swabable valve manufactured by Halkey Roberts, for example.

The second dome portion 104 includes a second port 110. The second port 110 may attach to a vial or container 300 (shown in FIG. 3) that contains fluid, as for enteral feeding, such as breast milk or nutrients, for example. When a vacuum is created in the first chamber 103, fluid from the container 300 is pulled into the expanding second chamber 105 through the second port 110. The connection between the second port 110 and the container 300 may be a threaded connection, for example, or may be any other suitable connection.

Alternatively, a special connector 112 may join the second port 110 to the container 300 to help prevent contamination of the port and/or connector. An example connector 112 of this type is described in detail in U.S. Application Ser. No. 61/367,228, (MBHB docket number 10-745), entitled "Enteral Feeding Connector and Assembly," filed on Jul. 23, 2010, and which is incorporated by reference herein in its entirety.

The first dome portion 102 further includes an aperture 114, which communicates with the first chamber 103. A regulator, such as regulator 116 shown in FIG. 3, is placed in the aperture 114 to control the speed at which the flexible membrane 106 moves back to its initial position, i.e., a position where there was no vacuum in the first chamber 103, and thus limit the fluid flow. The regulator 116 may comprise a dial, valve, or any other suitable regulator of air or fluid. Here, a plurality of interchangeable regulators may be used, such as regulators 116, 118, and 120, for example. Regulators 116, 118, and 120 may all have different configurations to allow air to enter the aperture 114 at different rates, thus regulating the flow of the fluid out of the second chamber 105. For example, when inserted into the aperture 114, regulator 116 may allow a larger stream of air to enter for a faster feeding rate; regulator 118 may allow a medium stream of air to enter for a medium feeding rate; and regulator 120 may allow a smaller stream of air to enter for a slower feeding rate. An "off" regulator position (as by rotating a regulator relative to an alignable air conduit structure) may also exist to prevent air passage, to maintain the fluid in the second chamber 105. It should be understood that other suitable regulator devices, including a single regulator adjusting to multiple flow rates, may be used with the pumping device of the present application, such as, for example, the regulator devices disclosed in U.S. Pat. No. 7,255,681.

Figure 2A:
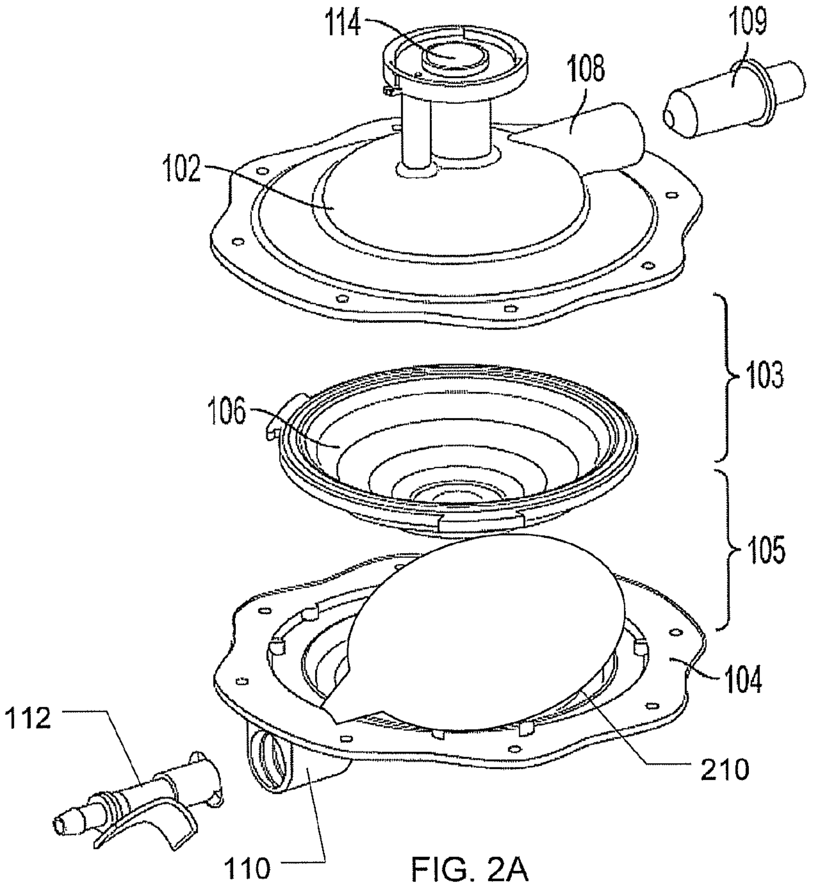
FIG. 2A is an exploded view of an alternative embodiment of the pumping device shown in FIG. 2.

In another embodiment, as shown in FIG. 2A, a flexible bag or balloon 210 may be placed within the second chamber 105. The bag 210 receives the fluid from the container 300 through second port 110. After use, the bag can be discarded and a new bag may be placed into the second chamber 105. Thus, the bag 210 allows the pumping device 100 to be reused without being cleaned. In one embodiment, the second port 110 may be formed as part of the bag 210. In yet another embodiment, shown in FIG. 2B, the bag 210 may be placed between the dome portions 102, 104 in place of the flexible membrane 106. In this embodiment, the bag 210 receives fluid through the second port 110, and functions similarly to the flexible member 106. Again, the second port 110 may be formed as part of the bag 210. In yet a further variation, bag 210 may come prefilled.

Figure 2B:
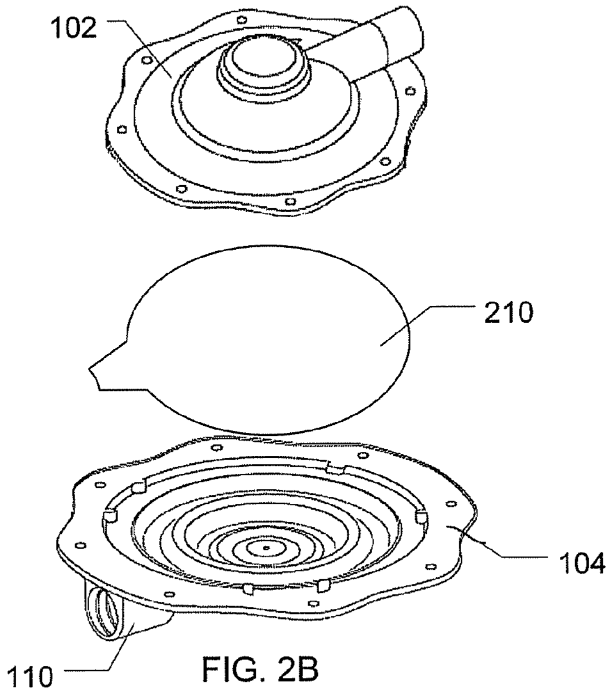
FIG. 2B is an exploded view of yet another alternative embodiment of the pumping device shown in FIG. 2.

The bag 210 will be placed within the device 100 of FIG. 2B, with the domes 102, 104 closed. An overpressure is then applied within the interior of the device 100, as by pushing the syringe plunger 201 into the barrel 203. A valve or metering device, such as could be provided in second port 110, would then provide outflow.

Referring to FIG. 3, in use, a piston or plunger 201 of the vacuum source or syringe 200 is pulled out from the syringe cylinder 203 in the direction of arrow 202. This creates a vacuum in the first space 103, and fluid is drawn out of the container 300 in the direction of arrow 302 through the second port 110, and into the second chamber 105 between the second dome portion 104 and flexible membrane 106.

Referring now to FIG. 4, the container 300 is then disconnected from the second port 110, and an enteral feeding tube 400 is connected to the second port 110, such as by the connector 112 (see, e.g., FIG. 1). A regulator 116, 118, and 120 has been previously selected to control the flow of fluid into the enteral feeding tube 400.

In operation, after a vacuum is introduced into the first port 108 of the pumping device 100 by the vacuum source 200, the one-way valve 109 located within the first port 108 closes upon removal of the vacuum source. The flexible membrane 106 has moved from the initial position to the expanded position, expanding the second space 105. At the same time, fluid from the attached container 300 has been pulled into the expanded second space 105 through second port 110. The flexible membrane 106 is the driving force to deliver fluid, and fluid flow is limited by the regulator 116, 118, or 120.

The enteral feeding tube 400 is attached to the second port 110. The regulator device is then actuated (e.g., rotated) to open an air channel to control the rate that the fluid is pumped from the expanded second chamber 105 into the enteral feeding tube 400, and eventually into the patient.

Figure 5:
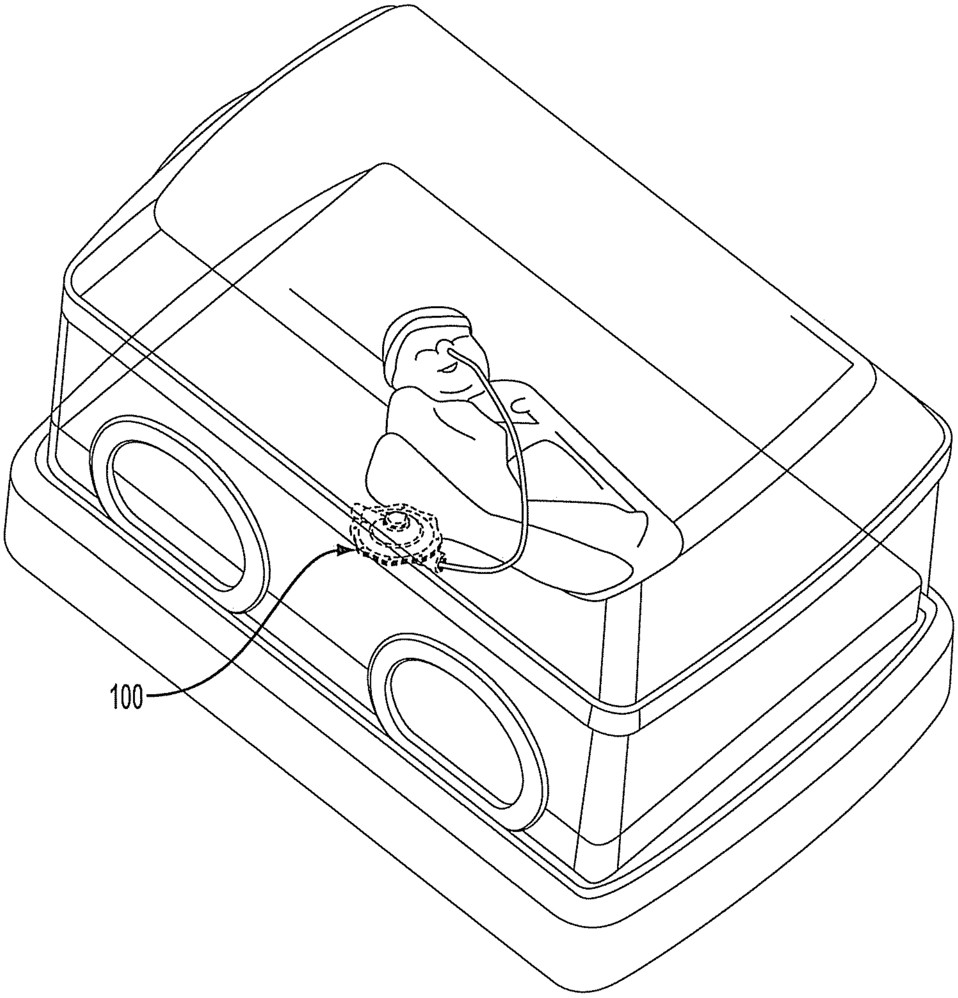
FIG. 5 is a perspective view of the pumping device shown in FIG. 1 in use with an enteral feeding tube in a patient (an infant) in a NICU bed.

As shown in FIG. 5, the pumping device 100 is lightweight and compact, and does not need to be plugged into an electrical outlet. It is not dependent on any electrical current. The pumping device can be placed very close to the patient, such as inside the incubator, eliminating the need for extension tubing. Thus, the enteral feeding tubing is a short tube.

In another embodiment, the pumping device 100 is pressurized by a pressure source, such as syringe 200 (being used to push rather than pull air or other fluid). The pressure source may be a syringe 200 containing the fluid for enteral feeding, for example, such as breast milk.

The pressure source 200 is connected to the second port 110 and the fluid from the pressure source is introduced into the second chamber 105. Using the structure like that of FIGS. 1 and 2, the flexible membrane 106 then expands toward the first dome portion 102, reducing the volume of the first chamber 103. A one-way valving can be placed in first port 108 to allow air out of the first chamber 103. The pressure source is then disconnected and an enteral feeding tube, such as enteral feeding tube 400, is connected to the second port 110, either directly or by the connector 112. The flow of fluid into the enteral feeding tube can then be metered by a regulating device, as described above. Alternatively, first port 108 is left open and a metering device is located near the second port 110 to regulate fluid flow out of the second port 100.

Figure 6:
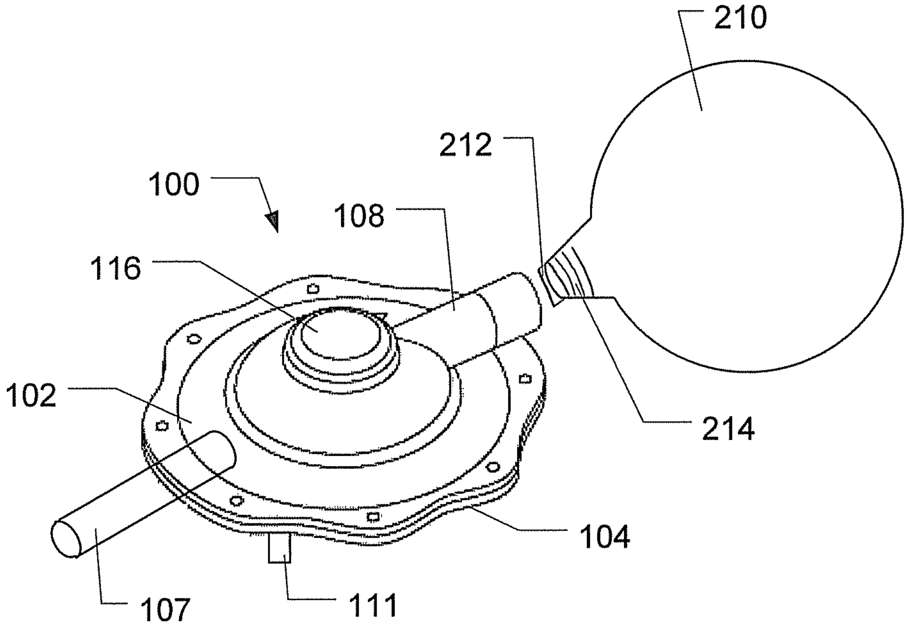
FIG. 6 is a perspective view of another embodiment of a pumping device of the present application.

In another embodiment, shown in FIG. 6, the pumping device 100 is pressurized with a positive pressure source, here a bag 210 containing fluid for enteral feeding, such as breast milk, for example. The bag 210 may have a cap 212 for closing the bag when not in use. The first dome portion 102 has a second or outflow port 107 in addition to the first or inflow port 108. The pressure source is connected to the first port 108 by a fastening mechanism 214, such as threads, for example, and squeezed or pushed to introduce the fluid into the first chamber 103. The flexible membrane 106 then expands toward the second dome portion 104, reducing the volume of the second chamber 105. An air vent 111 may be located on the second dome portion 104 to allow air out of the second chamber 105. Port 107 is initially closed during charging, as by appropriate valving and/or cover. The flow of fluid from the first chamber 103 out of the port 107 into an enteral feeding tube, bag, or bottle, can then be metered by a regulating device, as described above, or alternatively by a metering valve (not shown) located on the port 107 or associated with the enteral tubing 400.

Figure 7:
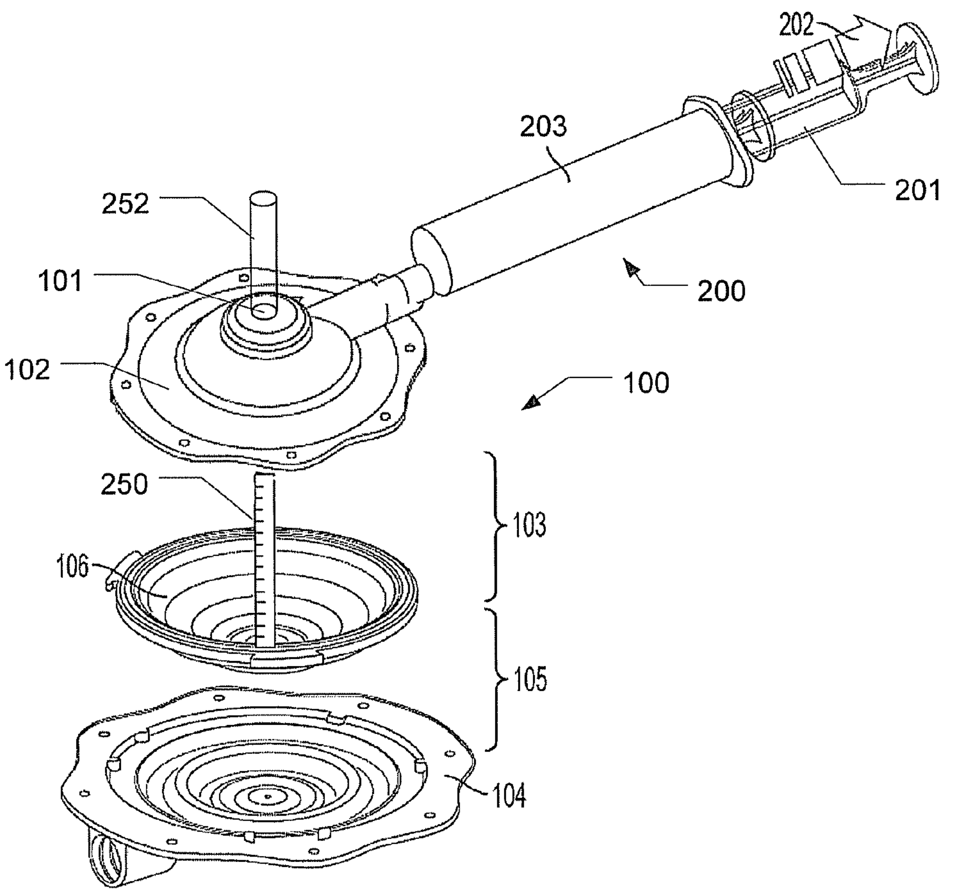
FIG. 7 is a perspective view of a volume indicator for use with the pumping device of FIG. 1.
Figure 7A:
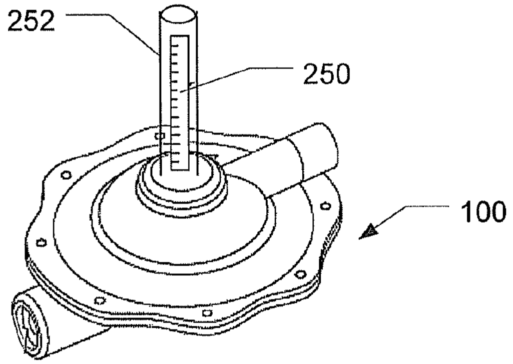
FIG. 7A is a perspective view of the volume indicator shown in FIG. 7 when the pumping device is in the filled position.
Figure 7B:
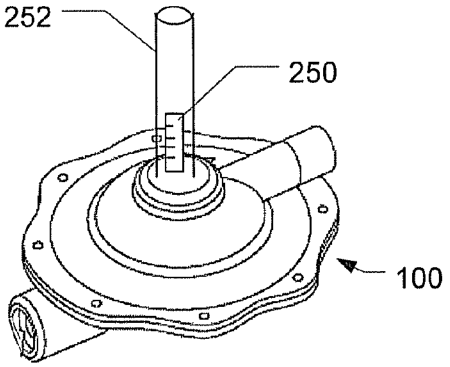
FIG. 7B is a perspective view of the volume indicator shown in FIG. 7 when the pumping device has been used for feeding.

Referring to FIG. 7, the pumping device 100 may further include a volume indicator 250 for measuring the movement of the diaphragm 106, thereby yielding an indication of volume of air (or liquid) within the chambers 103, 105 of the pumping device 100. The volume indicator 250 may extend through an aperture 101 in the first dome portion 102 down into the first chamber 103. The volume indicator 250 is attached to the membrane 106, and is moved upward or downward depending upon the movement of the diaphragm 106. The upper portion of the volume indicator 250 is enclosed by a clear cylindrical case or cover 252 to seal the volume indicator 250 with the chamber 103. FIG. 7A shows the pumping device 100 of FIGS. 1 and 2 using an indicator 250, in a filled position when little air is present in the chamber 103, and FIG. 7B shows the pumping device 100 in a “used” position, when the second chamber 105 has had outflow.

Figure 8:
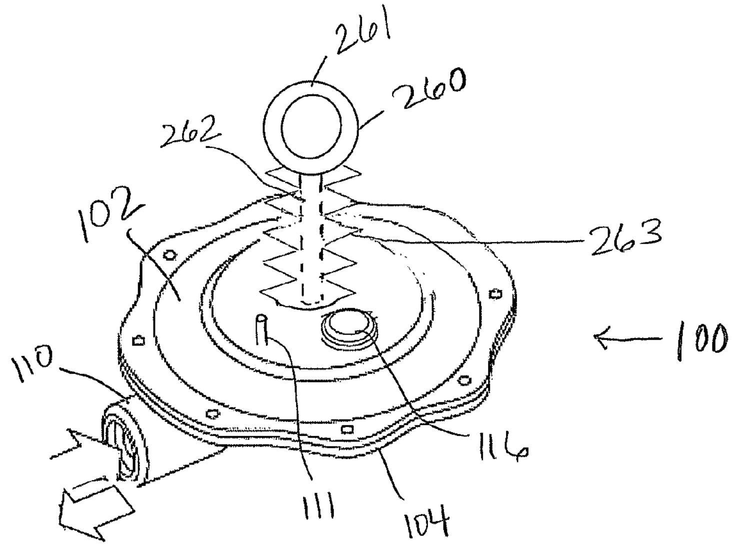
FIG. 8 is a perspective view of yet another embodiment of a pumping device of the present application.

Another embodiment of the pumping device 100 is shown in FIG. 8. In this embodiment, a pull tab 260 is provided on the first dome portion 102. The pull tab 260 is attached to the diaphragm 106 of a device 100 such as depicted in FIGS. 1 and 2 (modified for the pull tab). Pull tab 260 has a ring 261 on a shaft 262 which reciprocates within a bellows or sleeve 263. The sleeve 263 isolates the shaft and seals it with chamber 103. A regulator, such as regulator 116, 118, or 120, may also be used to control the speed at which the flexible membrane 106 moves back to its initial position, i.e., a position where there was no vacuum in the first chamber 103. The first dome portion 102 also includes a one-way air vent 111 for allowing air out of the first chamber 103 when the pull tab 260 is pulled. Port 110 is used both for inflow and outflow.

Figure 9:
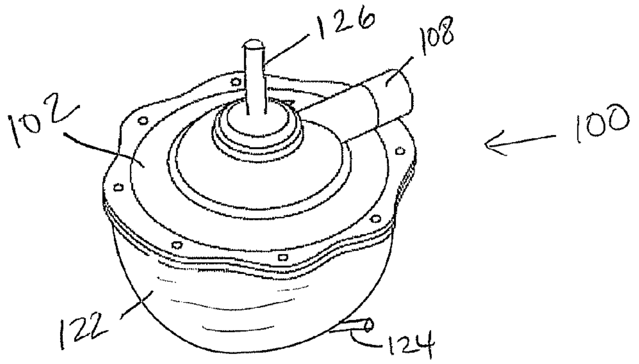
FIG. 9 is a perspective view of yet another embodiment of a pumping device of the present application.

In yet another embodiment of the pumping device, shown in FIG. 9, the second dome portion is made of a flexible, stretchable material, such as a balloon material, thereby creating a flexible bottom portion 122. In this embodiment, fluid or milk is introduced into the first dome portion 102 through first port 108. A membrane 106 may separate dome portion 102 from the bottom portion 122, creating a volume 103 for the feeding liquid. Alternatively, the fluid or milk may already be present within the pumping device 100, and first port 108 may not be present on the first dome portion 102. Air is then introduced through a lower port 124 in the flexible bottom 122, inflating the bottom portion 122 and creating a compressive force. This will be used to drive the fluid out of an upper port 126 in the first dome portion 102. External tubing 400 would be connected to port 126, along with suitable valving/metering for outflow control.

Figure 10:
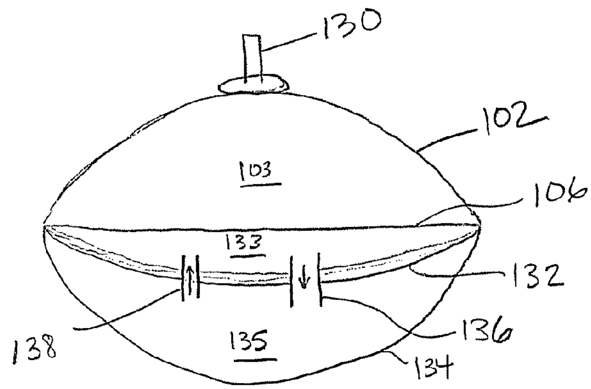
FIG. 10 is a cross-sectional view of yet another embodiment of a pumping device of the present application.

FIG. 10 shows yet another embodiment of the pumping device 100. In this embodiment, the pumping device is controlled by liquid instead of air. Fluid or liquid control may provide for more consistency and enhanced flow control of the pumping device 100. The first dome portion 102 includes a port 130, which may be a two-way port through which the feeding fluid or milk may flow into and out of. Alternatively, separate ports may be provided for the flow of feed fluid into and out of the first dome portion 102. The first dome portion 102 is enclosed and has a first chamber 103. A divider 132 is between the first and second dome portions 102, 104. A different liquid, such as water, for example, is present in a chamber 133 located between the divider 132 and a dome portion 134 on the other side of the first membrane 132. The dome portion 134 is made of a flexible material. The dome portion 134 defines an expansible chamber 135.

The divider 132 includes a large one-way valve 136 and a small one-way valve 138. The large one-way valve 136 allows for the flow of the liquid from the chamber 133 to the chamber 135 once feed fluid is introduced into the first dome portion 102. The flow of the liquid into the chamber 135 causes the chamber to expand. The build-up of liquid and therefore pressure in the chamber 135 then can be used to cause the liquid to flow back into the chamber 133 more slowly through the small one-way valve 138. The liquid flows back into the chamber 133 with feed and flow from chamber 103 as diaphragm 106 returns to its rest position, while pushing the feed fluid in the first chamber 103 out of port 130 and into a feeding tube to a patient. In an alternate embodiment, a pull tab 260 like that described with respect to FIG. 8 could be adapted for use in pulling diaphragm 106 into charging position in this embodiment of FIG. 10.

It should be understood that any of the embodiments described above may be driven with either positive or negative pressure, or a combination of both, as would be known and understood by those skilled in the art. Similarly, ports may be either one-way or two-way ports.

Figure 11:
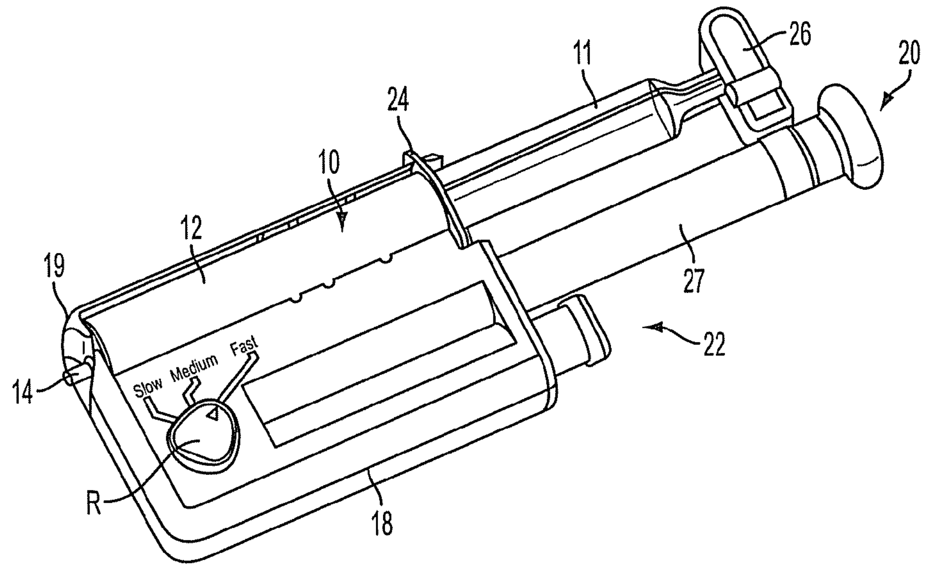
FIG. 11 is a perspective top view of yet another pumping device according to the present application.

FIG. 11 shows some of the basic elements of the pump drive and enteral feeding system of another embodiment of the present invention. Components include a container for delivery of the enteral feed (liquid), here a standard-type feeding syringe 10. Syringe 10 has a plunger 11 in a barrel 12, with a tip 14. Tip 14 will connect with enteral tubing 15 (FIG. 14), for instance, in a well-known manner.

Syringe 10 is mounted in a casing 18. Also mounted within casing 18 is the spring pump drive mechanism, which has a driving piston device 20 and a damping or driven piston device 22. While this embodiment uses hydraulics to control the spring return in its operation, some other fluid could be used, such as in a pneumatic adaptation.

Figure 12:
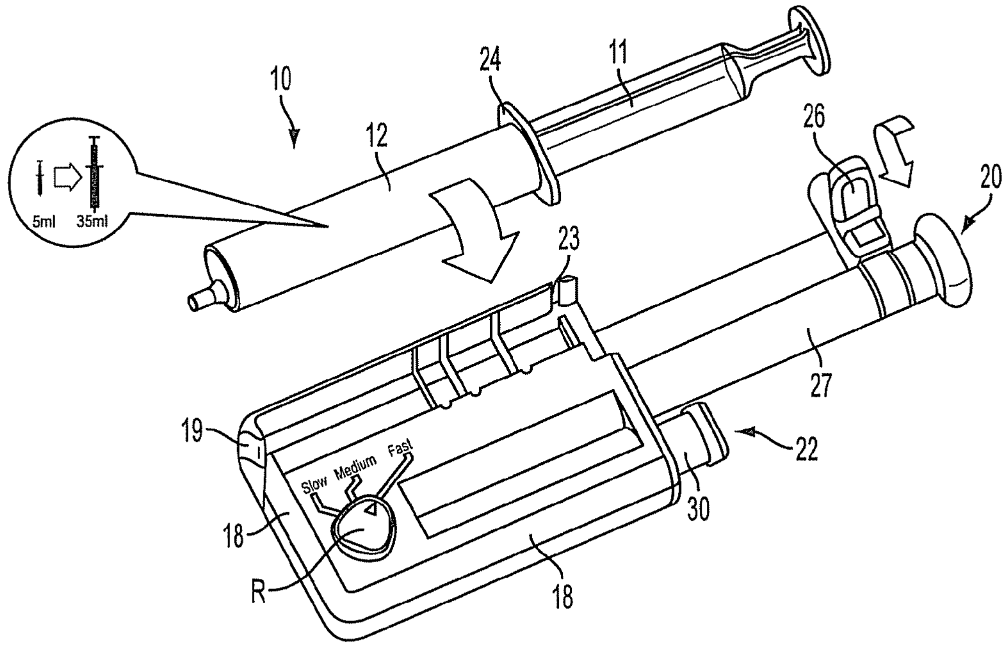
FIG. 12 is a perspective view like that of FIG. 11 showing how a syringe is loaded into the pumping device.
Figure 13:
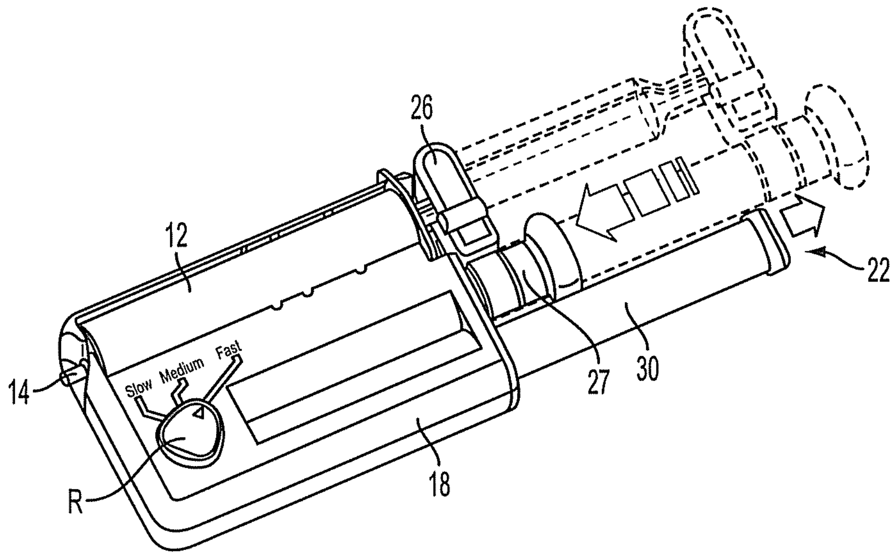
FIG. 13 is a similar perspective view to that of FIG. 11, but showing how the elements have moved in the course of discharge of the syringe.

The two piston devices are in fluid communication in a manner to be hereafter described. With reference to FIG. 12 for the moment, however, it will be seen that a syringe 10 with feed therein has its plunger 11 pulled outwardly from the barrel 12. The syringe in this condition is then placed in its compartment 19 within the casing 18. It may be held in place by a notch 23 formed in the compartment within which is received a flange 24 on the barrel 12. Tip 14 extends from the front of the compartment 19.

A connector element 26, such as a clamp, serves to fix the plunger 11 to a driving piston cylinder 27 of the driving piston device 20. The plunger is thus slaved for movement with the piston cylinder 27.

Figure 14:
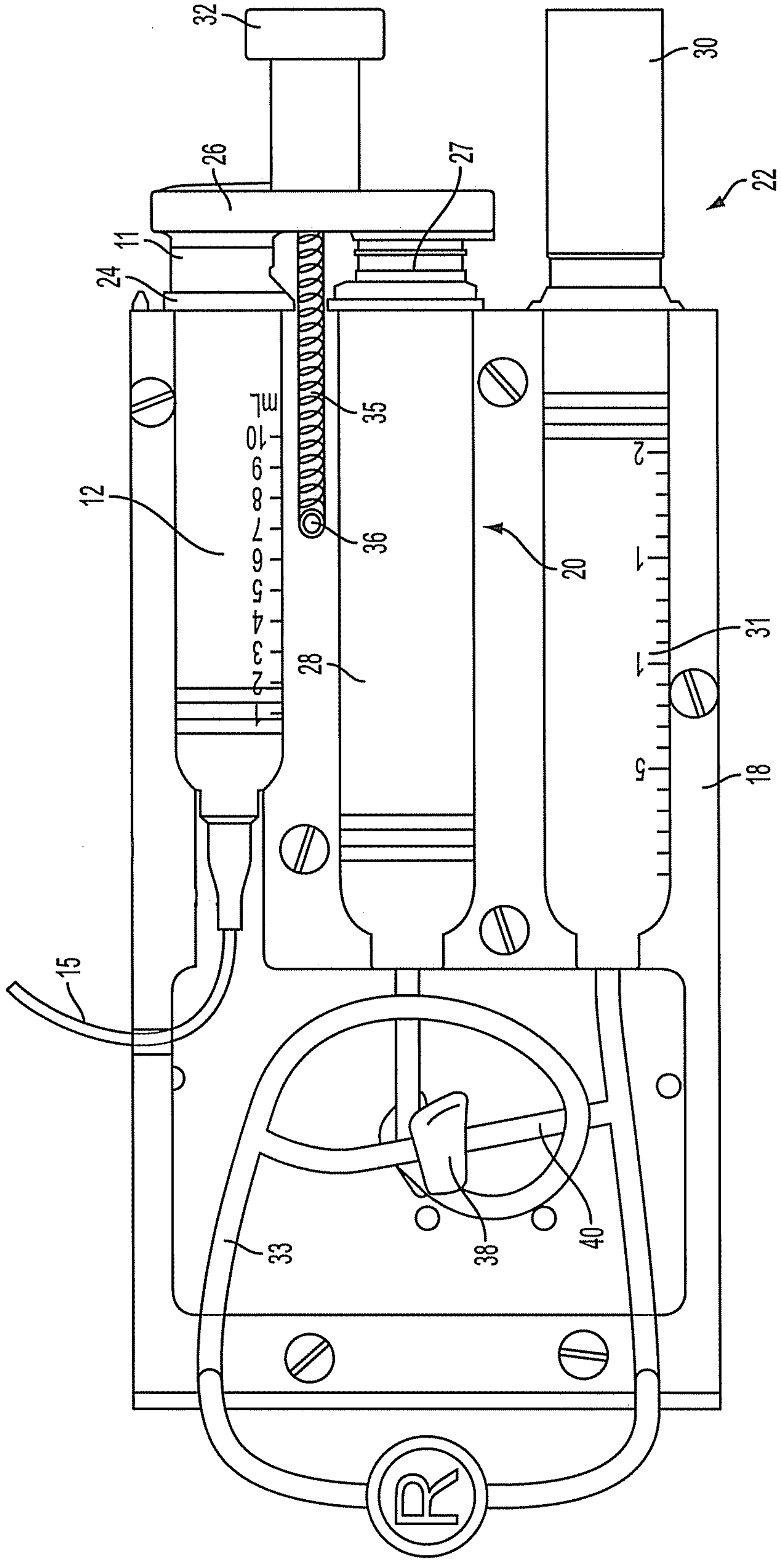
FIG. 14 is a top plan view of an embodiment using a mechanism like that represented in FIGS. 11 through 13, detailing the tubing arrangement.

Referring now to FIG. 14, driving piston cylinder 27 moves within driving barrel 28, which is mounted in the casing 18. In this embodiment, a standard syringe was adapted to function as the driving piston device 20, but this is merely an illustrative example. Likewise, a standard syringe was adapted to function as the driven piston device 22, which has a driven piston 30 that moves within its barrel 31, which is likewise just an illustrative example. A tube 33 is connected to the tip of the barrel 28 and to the tip of the barrel 31, forming a conduit structure therebetween. A liquid, such as water, is contained within the closed hydraulic system thus formed by the piston devices and the tube 33. When the driving piston cylinder 27 of driving piston device 20 is pulled outwardly (out relative to its barrel), fluid moves into driving piston barrel 28 through tube 33, and driven piston cylinder 30 moves inwardly relative to its barrel, in balance of the system.

The initial energy to move the piston cylinders is supplied by the user grasping the handle 32 of the driving piston cylinder and pulling it outwardly. This pulls it against a spring 35, which is fixed at one end to the casing 18 at point 36, and at the other end to the connector element 26, thereby extending the spring 35, and "cocking" the pump mechanism. The spring 35 may be a constant force spring, for example. When the handle 32 is then released, the spring 35 serves to pull the driving piston inwardly in its barrel, moving fluid into driven piston barrel 31, pushing driven piston 30 outwardly. A regulator device R is in-line with tube 33. The regulator R can be of any standard type through which liquid may be variably metered. The regulator is set to the desired rate of feeding, so that the spring 35 slowly (typically) pulls the driving piston cylinder 27 with its slaved syringe plunger 11 inwardly relative to their barrels, with feed thereby being administered from the syringe, as its plunger 11 moves inwardly in the barrel 12.

Figure 15:
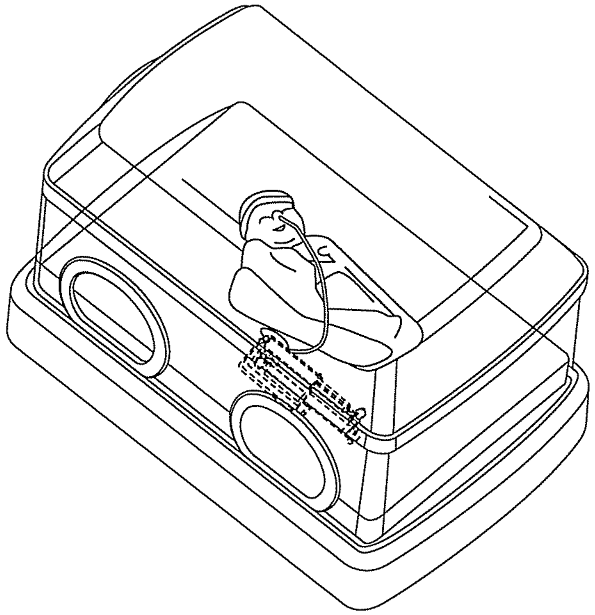
FIG. 15 is a perspective schematic view of the pumping device shown in FIG. 11 and enteral feeding system in a NICU bed.

In order to facilitate resetting of the system, a one-way valve mechanism 38, such as a duckbill valve, is connected in another tube 40 forming a short-circuit for the quick return of fluid to the driving piston device 20 (thereby substantially or completely bypassing return through the regulator R). FIG. 15 shows the portable pumping mechanism and enteral feeding system in place in a NICU unit. The enteral feeding tube connected to the portable pump is short to allow the portable pump to be positioned close to the patient, and even within the incubator.

Thus, while the invention has been described herein with relation to certain embodiments and applications, those with skill in this art will recognize changes, modifications, alterations and the like which still come within the spirit of the inventive concept, and such are intended to be included within the scope of the invention. For instance, while the vacuum source and pressure source have been described as syringes or bags, other vacuum sources or pressure sources may be used.

What is claimed is:

1. A pumping device for attachment to an enteral feeding tube comprising:

a first portion attached to a second portion;

a flexible membrane located between the first portion and the second portion, thereby forming a first chamber between the first portion and the flexible membrane, and a second chamber between the second portion and the flexible membrane;

a vacuum source connected to the pumping device to create a vacuum in the first chamber and to draw liquid feed into the second chamber; and a regulator connected to the pumping device;

wherein when the vacuum source is disconnected from the pumping device, the regulator is actuated to open an air channel in the first portion to control a rate at which the liquid feed is pumped out of the second chamber for delivery to the enteral feeding tube.

2. The pumping device of claim 1 further comprising a bag positioned in the second chamber for receiving the fluid.

3. The pumping device of claim 1 wherein the flexible membrane is a bag.

4. The pumping device of claim 1 wherein the enteral feeding tube is short to allow the pumping device to be positioned close to the patient.

5. The pumping device of claim 1 wherein the pumping device is non-electrically driven.

6. The pumping device of claim 1 further comprising a volume indicator positioned on the pumping device for measuring the amount of fluid or air in the pumping device.

7. The pumping device of claim 1 wherein the vacuum source is a syringe.

8. The pumping device of claim 1 wherein the vacuum source is a pull tab.

9. The pumping device of claim 1 wherein the first portion includes a first port having a one way valve, the vacuum source being connected to the first port.

10. A pumping device for enteral feeding comprising:

a housing;

a flexible membrane located within said housing and defining a first chamber on one side of said flexible membrane and a second chamber on another side of said flexible membrane;

a first port in said housing communicating with said first chamber and a second port in said housing communicating with said second chamber, said first port being connectable with a source of vacuum, said second port being connectable with a source of feed for a person; and valving associated with said ports controlling flow through a respective port;

wherein when a vacuum is drawn in said first chamber, said flexible membrane moves to decrease a volume in said first chamber and serves to draw feed into said second chamber from said source of feed connected to said second port, with said flexible member providing a driving force for forcing enteral feed out of said second chamber through said second port as said flexible membrane returns to a rest position.

11. A pumping device specially adapted for use in delivering feed through enteral tubing to a person, comprising:

a first portion attached to a second portion;

a flexible membrane located between the first portion and the second portion, thereby forming a first chamber between the first portion and the flexible membrane, and a second chamber between the second portion and the flexible membrane;

a first port communicating with the first chamber and a second port communicating with the second chamber;

a pressure source connectable to the first port to introduce fluid into the first chamber, thereby moving the membrane into the second chamber and reducing the volume of the second chamber;

tubing connectable to the first port for delivering fluid to a person enterally; and a regulator connected to the pumping device, the regulator controlling a rate at which the fluid is let out of the first chamber as the flexible membrane is allowed to move back to a rest position thereby forcing the fluid out of the first port.

12. The pumping device of claim 11 wherein the pressure source is a syringe.

13. The pumping device of claim 11 wherein the pressure source is a bag.

14. The pumping device of claim 11 wherein the fluid flows out of the first chamber through a third port communicating with the first chamber.

15. The pumping device of claim 11 wherein an air vent is positioned on the second portion to release air from the second chamber.

16. A pumping device comprising:

a housing having a rigid first portion connected to a flexible second portion, the flexible second portion having a sidewall connected to the rigid first portion defining a first chamber with the rigid first portion and a second chamber with the flexible second portion, wherein fluid for feeding is located in the first chamber; and a first port communicating with the first chamber and a second port communicating the second chamber;

wherein when air is introduced into the flexible second portion through the second port, the flexible second portion inflates, thereby creating a force to drive fluid for feeding out of the first port in the rigid first portion.

17. A pumping device comprising:

a first portion having at least one port and a first chamber;

a flexible second portion connected to the first portion; and a membrane located between the first portion and the flexible second portion, thereby forming a second chamber between the first portion and the membrane, and a third chamber between the flexible second portion and the membrane, the membrane further including first and a second one-way valves;

wherein when feed fluid is introduced into the first chamber, liquid present in the second chamber is forced through the first one-way valve into the third chamber, then forced through the second one-way valve back into the second chamber, which creates pressure in the second chamber to force the feed fluid out of the first chamber.

18. A pump comprising:

an expansible chamber device having a member movable between sides of a sealed housing defining a first and a second chamber, the member having a rest position and a driving position, with the member being biased toward the rest position when in the driving position;

valving associated with each chamber to permit the member to move within the housing and thereby expand a volume in one chamber while decreasing a volume in the other chamber;

at least one port communicating with the first chamber; and a bag having fluid therein for feeding a person in an enteral feeding arrangement, the bag having an outlet for connection to the port of the first chamber, wherein when the bag is connected to the port and fluid is forced by hand from the bag into the first chamber, the fluid then provides a force on the movable member to push the movable member to the driving position, the bias on the movable member then operating to move fluid out of the first chamber through the one port or another port communicating with the first chamber.

19. A pumping device for enteral feeding comprising:

a housing;

a flexible member located within said housing and defining a first chamber on one side of said flexible member and a second chamber on another side of said flexible member;

a first port in said housing communicating with said first chamber and a second port in said housing communicating with said second chamber;

valving associated with said ports controlling flow through a respective port;

wherein when a pressure differential is formed between said chambers, said flexible member moves to decrease a volume in one chamber and serves to draw feed into the other chamber from said source of feed connected to the other chamber, with said flexible member providing a driving force for forcing feed out of the feed-filled other chamber as said flexible member returns to a rest position; and a volume indicator device, said volume indicator device having an elongate element with indicia thereon which are associated with the volume present in a chamber, said elongate element being attached to said flexible member at one end and extending through a side of said housing so as to be visible to a person viewing said pumping device.

20. The pumping device of claim 19, further including an enclosure surrounding said elongate element and providing a sealed enclosure with a chamber within which said elongate element extends, said enclosure having a transparent region for viewing of said element.

21. A pumping device for enteral feeding comprising:

an expansible chamber device defining a first and a second chamber defined by a movable member between the chambers having a rest position and a driving position, with the member being biased toward the rest position when in the driving position;

valving associated with each chamber to permit the movable member to move within the expansible chamber device and thereby expand a volume in one chamber while decreasing a volume in the other chamber;

at least a first port communicating with the first chamber and a second port communicating with the second chamber;

a regulating mechanism controlling outflow from the first chamber; and a bag being received within the first chamber, the bag receiving fluid therein for feeding a person in an enteral feeding arrangement, the bag having a part connectable to the first port of the first chamber when located in the first chamber;

wherein when a vacuum is applied to the second port, the movable member is moved to decrease a volume in the second chamber and place the movable member in the driving position while causing feed fluid to flow into the bag; and whereupon operation of the regulating mechanism causes the movable member to return toward the rest position through the bias while causing feed fluid to flow out of the bag through the first port.

22. The pumping device of claim 21 wherein the bag is disposable.

23. A pumping device for enteral feeding comprising:

a housing having an interior which is accessible in a first condition and sealed in a second condition;

a first outflow port communicating with said interior and a second pressure port communicating with said interior;

a regulating mechanism controlling a rate of outflow from said first outflow port; and a bag being received within said first chamber, said bag being filled with fluid therein for feeding a person in an enteral feeding arrangement, said bag having a part connectable to said first outflow port when located in said interior for outflow from said bag;

wherein when a positive pressure from a source is applied to said interior through said second pressure port in said second condition and said port is closed with said pressure source then removed, said interior is pressurized and provides a driving force to compress said bag causing feed fluid to flow from said bag through said first outflow port upon operation of said regulating mechanism.

24. A pumping device for enteral feeding comprising:

a housing;

a flexible member located within said housing and defining a first chamber on one side of said flexible member and a second chamber on another side of said flexible member, said flexible member having a rest position and a drive position defined by a bias toward said rest position;

at least a first port in said housing communicating with said first chamber;

valving associated with said first port controlling flow through said first port; and a puller having one end connected to said flexible member on said another side of said flexible member and within said second chamber, and another end of said puller extending out of said housing, said another end of said puller being graspable by a person;

wherein when said puller is pulled in a direction away from said housing to said drive position, said flexible member moves to decrease a volume in said second chamber and serves to draw feed into said first chamber from a source of feed connected to said first chamber using said at least first port, with said flexible member providing a driving force for forcing enteral feed out of the feed-filled first chamber as said flexible member returns to a rest position.

25. A pumping device for enteral feeding comprising:

a housing;

a movable member mounted to said housing and defining a first chamber with said housing using one side of said movable member, said movable member having a rest position and a drive position defined by a bias toward said rest position;

at least a first port in said housing communicating with said first chamber;

valving associated with said first port controlling flow through said first port; and a puller having one end connected to said movable member on another side of said movable member, said another end of said puller being graspable by a person;

wherein when said puller is pulled in a direction away from said housing to said drive position, said movable member moves to increase a volume in said first chamber and serves to draw feed into said first chamber from a source of feed connected to said first chamber using said at least first port, with said movable member providing a driving force for forcing enteral feed out of the feed-filled first chamber as said movable member returns to a rest position.

26. The pumping device of claim 25 wherein said movable member is made of a flexible material, said bias being provided by stretching said flexible material to said drive position.

27. The pump of claim 18 further comprising a regulating mechanism controlling outflow from the first chamber.

28. The pumping device of claim 10 further comprising a bag positioned in the second chamber for receiving the fluid.

29. The pumping device of claim 10 wherein the flexible membrane is a bag.

30. The pumping device of claim 10 wherein the pumping device is non-electrically driven.

31. The pumping device of claim 10 wherein the vacuum source is a syringe.

* * * * *